(12) United States Patent
Walter

(10) Patent No.: US 11,912,576 B2
(45) Date of Patent: Feb. 27, 2024

(54) PROCESS AND PLANT FOR PRODUCING A PURIFIED AND CONVERTED SYNTHESIS GAS

(71) Applicant: L'Air Liquide, Société Anonyme pour l'Etude et l'Exploitation des Procédés Georges Claude, Paris (FR)

(72) Inventor: Stefan Walter, Griesheim (DE)

(73) Assignee: L'Air Liquide, Société Anonyme pour l'Etude et l'Exploitation des Procédés Georges Claude, Paris (FR)

( * ) Notice: Subject to any disclaimer, the term of this patent is extended or adjusted under 35 U.S.C. 154(b) by 925 days.

(21) Appl. No.: 16/668,068

(22) Filed: Oct. 30, 2019

(65) Prior Publication Data
US 2020/0131035 A1  Apr. 30, 2020

(30) Foreign Application Priority Data
Oct. 31, 2018 (EP) ..................................... 18020567

(51) Int. Cl.
| | | |
|---|---|---|
| C01B 3/38 | (2006.01) | |
| C01B 3/36 | (2006.01) | |
| C01B 3/56 | (2006.01) | |
| C07C 29/151 | (2006.01) | |

(52) U.S. Cl.
CPC ................ *C01B 3/382* (2013.01); *C01B 3/36* (2013.01); *C01B 3/56* (2013.01); *C07C 29/1518* (2013.01); *C01B 2203/0233* (2013.01); *C01B 2203/0244* (2013.01); *C01B 2203/0255* (2013.01); *C01B 2203/043* (2013.01); *C01B 2203/0405* (2013.01); *C01B 2203/046* (2013.01); *C01B 2203/048* (2013.01); *C01B 2203/061* (2013.01); *C01B 2203/1241* (2013.01)

(58) Field of Classification Search
CPC ...................................................... C01B 3/382
See application file for complete search history.

(56) References Cited

U.S. PATENT DOCUMENTS

| | | | |
|---|---|---|---|
| 3,064,029 A | 11/1962 | White | |
| 5,221,524 A * | 6/1993 | Eguchi | ...................... C01B 3/32 423/655 |
| 2009/0183431 A1* | 7/2009 | Smit | .......................... C10J 3/84 48/197 R |

(Continued)

FOREIGN PATENT DOCUMENTS

WO  WO 2009 065841  5/2009

OTHER PUBLICATIONS

European Search Report and Written Opinion for corresponding EP 18020567, dated Feb. 18, 2019.

*Primary Examiner* — Paul A Wartalowicz
(74) *Attorney, Agent, or Firm* — Elwood L. Haynes

(57) ABSTRACT

An integrated process for producing a purified and converted synthesis gas and a corresponding plant including initially converting in a synthesis gas generation stage a carbon-containing input material into a raw synthesis gas which in a subsequent CO conversion zone is altered in respect of its $H_2/CO$ ratio and finally sent to a gas scrubbing zone operating according to a physical gas scrubbing process with methanol as the absorption medium in which the content of unwanted gas constituents, in particular of acidic gas constituents, in the synthesis gas is reduced.

7 Claims, 2 Drawing Sheets

(56) References Cited

U.S. PATENT DOCUMENTS

2009/0246118 A1* 10/2009 Drnevich .............. C10J 3/466
　　　　　　　　　　　　　　　　　　　　　423/650
2010/0005965 A1* 1/2010 Kodde .................. B01D 53/04
　　　　　　　　　　　　　　　　　　　　　95/148
2019/0022582 A1* 1/2019 Navid .................... B01J 35/06

* cited by examiner

PROCESS AND PLANT FOR PRODUCING A PURIFIED AND CONVERTED SYNTHESIS GAS

CROSS REFERENCE TO RELATED APPLICATIONS

This application claims the benefit of priority under 35 U.S.C. § 119 (a) and (b) to European Patent Application No. EP 18020567.6, filed Oct. 31, 2018, the entire contents of which are incorporated herein by reference.

BACKGROUND

Field of the Invention

The invention relates to a process for producing a purified and converted synthesis gas which comprises not only the essential synthesis gas constituents hydrogen ($H_2$) and carbon monoxide (CO) but also acidic secondary constituents such as carbon dioxide ($CO_2$) and hydrogen sulfide ($H_2S$) and also trace constituents such as for example carbonyl sulfide (COS), ammonia ($NH_3$), hydrogen cyanide (HCN), mercaptans (RSH) and metal carbonyls, in particular iron and nickel carbonyls. It comprises initially converting in a synthesis gas generation stage a carbon-containing input material into a raw synthesis gas which in a subsequent CO conversion zone is altered in respect of its $H_2$/CO ratio and finally sent to a gas scrubbing zone operating according to a physical gas scrubbing process with methanol as the absorption medium in which the content of unwanted gas constituents, in particular of acidic gas constituents, in the synthesis gas is reduced.

The invention likewise relates to a plant for performing the process according to the invention.

Prior Art

On account of its great importance as an input material for numerous chemical syntheses, for example chemical industry feedstocks such as methanol or ammonia, the production of synthesis gas, i.e. gas mixtures comprising as their essential constituents hydrogen ($H_2$) and carbon monoxide (CO), has long been known and has been the subject of a great deal of discussion in the literature.

Reactants used for synthesis gas generation are generally carbon-containing input materials or input material mixtures which may be in solid, liquid or gaseous states of matter. Examples here include coal in lump form or powder form, biomass, crude oil fractions, pyrolysis oils, biogas or natural gas. For conversion of non-gaseous input materials into synthesis gas, the operation is often described as gasification, whereas, when using natural gas, it is more usual to refer to reforming, for example—depending on the process mode—to steam reforming or autothermal reforming (ATR) or—in the absence of solid catalysts—to partial oxidation (PDX).

Initially obtained as the product of synthesis gas generation is a raw synthesis gas which in many cases is to be altered in respect of its $H_2$/CO ratio and is to be freed of certain unwanted by-products and trace constituents to make it suitable as an input for downstream process or synthesis stages.

Adjustment of the $H_2$/CO ratio is via the CO conversion reaction also known as the water-gas shift reaction (WGS) or CO shift reaction according to the reaction equation $$CO + H_2O \rightleftharpoons CO_2 + H_2$$

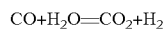

Addition of steam causes the CO to react to afford $CO_2$ and $H_2$. Due to the reaction enthalpy of −41.2 kJ/mol, increasing temperature shifts the chemical equilibrium from the reaction products towards the reaction reactants. Depending on the employed reaction temperature, the reaction is referred to as a high temperature shift (HTS), medium temperature shift (MTS) or low temperature shift (LTS).

Depending on the type of catalysts employed, it is further also possible to perform the shift reaction with unpurified raw synthesis gas. This process is referred to as raw gas shift or else—on account of the acidic gas constituents, namely $CO_2$ and $H_2S$—as sour gas shift. Said process may also be performed with raw synthesis gases containing significant amounts of sulfur, soot or condensable hydrocarbons. A typical application is the CO conversion of raw gases from heavy oil gasification that have not been cooled and desulfurized but rather have only been quenched in the hot state to add the necessary steam and to remove soot. A further typical application is the conversion of carbon monoxide into raw gases from pressure coal gasification which contain not only sulfur but also saturated and unsaturated hydrocarbons, including tars. For conversion of both raw gas types, catalysts based on cobalt/molybdenum have proven particularly advantageous. These are sulfur-resistant or achieve their full activity only in the presence of sulfidic sulfur. For instance, the carbon monoxide content (about 45 vol %) of a raw gas from the partial oxidation of heavy oil that enters the CO shift reactor at about 250° C. and has a steam/dry gas ratio of about 0.8 can be reduced to about 1.6 vol % in a two-stage CO shift reactor system having a cobalt/molybdenum catalyst. The heat liberated by the reaction enthalpy is used for example for generating high-pressure and low-pressure steam and for preheating feed water.

Processes for separation of unwanted concomitants from raw synthesis gases by physical or chemical absorption or gas scrubbing are well-known from the prior art. Thus such processes may be used to safely remove down to the trace range unwanted, acidic constituents of raw synthesis gases produced by gasification or reforming of carbon-containing inputs, for example carbon dioxide ($CO_2$) and hydrogen sulfide ($H_2S$) but also further constituents such as carbonyl sulfide (COS), hydrogen cyanide (HCN) or mercaptans (RSH), from the wanted synthesis gas constituents hydrogen ($H_2$) and carbon monoxide (CO). One known and often used process is the Rectisol process which is likewise described in principle in the abovementioned literature.

In the Rectisol process the abovementioned unwanted disruptive components are absorbed by cold methanol, i.e. methanol cooled significantly below ambient temperature, as an absorbent or scrubbing medium, wherein intensive mass transfer between the raw gas and the scrubbing medium/absorption medium takes place in an absorber column also known as a scrubbing column. The solubility of the unwanted gas constituents increases drastically with decreasing temperature of the methanol and increasing pressure while remaining practically constant for hydrogen and carbon monoxide. Methanol additionally has the advantage of still retaining a low viscosity and thus good mass and heat transfer properties even at temperatures down to −75° C.

The methanol laden with the disruptive components and used as absorption medium is circulated through regeneration apparatuses in the Rectisol process. In the regeneration apparatuses the laden methanol is freed from the absorbed gases by physical means. Thus, in a first regeneration step $CO_2$ is removed from the laden methanol absorption medium by decompression (so-called flash regeneration) and/or stripping with a gas, for example nitrogen. In a further or alternative regeneration step the sulfur-containing gases, COS and $H_2S$, are driven off by heating (so-called hot regeneration).

In the Rectisol process a distinction is made between the standard process and the selective Rectisol process. In the standard Rectisol process the concomitant gases COS/$H_2S$ and the $CO_2$ are removed from the raw synthesis gas together in one absorption step. By contrast, in the so-called selective Rectisol process the sulfur-containing concomitant gases COS/$H_2S$ and the $CO_2$ are respectively removed from the raw synthesis gas in separate consecutive absorption steps.

After passing through what are normally several regeneration steps several sub-streams of the absorption medium, i.e. in the Rectisol process classically the methanol, freed of the disruptive components are recycled to the absorber column. The absorption medium regenerated by hot regeneration has the highest purity and is therefore used for fine scrubbing/fine absorption of previously prepurified synthesis gas; it thus constitutes the final scrubbing stage before the purified synthesis gas exits the absorber column typically at the upper end thereof as pure synthesis gas.

In order to prevent an accumulation of trace components or else of water in the methanol absorption medium it is necessary to continuously discharge from the gas scrubbing process a small stream of the absorption medium laden with the trace components or other unwanted constituents. Thus US patent publication U.S. Pat. No. 3,064,029 A describes an absorption process for purifying synthesis gas with methanol as the absorption medium, wherein a water-laden methanol stream is discharged and the water concentration is thus limited to 2 mol %.

This discharge stream is referred to as a purge stream or bleed stream. It may subsequently be disposed of by incineration in a suitable incineration plant or by a disposal service provider. However, the disadvantage is that this entails costs, especially if a suitable incineration plant is not available at all or at sufficient scale in the integrated plant concerned. A further disadvantage is that the purge stream is utilized only thermally and not as a feedstock during the incineration.

SUMMARY

The present invention accordingly has for its object to specify a process and a plant which avoid the recited disadvantages of the prior art and in particular make it possible to produce a purified and converted synthesis gas, wherein the methanol purge stream obtained from the gas scrubbing with methanol as the absorption medium is disposed of or utilized more efficiently.

Process for producing a purified and converted synthesis gas containing hydrogen ($H_2$) and carbon monoxide (CO), comprising the following process steps:
  a) providing a carbon-containing gasification or reforming input stream and introducing said stream into a synthesis gas generation stage,
  b) reacting the carbon-containing gasification or reforming input stream in the synthesis gas generation stage under synthesis gas generation conditions to afford a raw synthesis gas product stream which contains not only the primary constituents $H_2$ and CO but also carbon dioxide ($CO_2$) and hydrogen sulfide ($H_2S$) as acidic synthesis gas constituents as well as secondary and trace components such as carbonyl sulfide (COS), ammonia ($NH_3$), hydrogen cyanide (HCN), mercaptans (RSH), metal carbonyls, discharging the raw synthesis gas product stream from the synthesis gas generation stage,
  c) introducing the raw synthesis gas product stream into a CO conversion zone (CO shift zone), converting the raw synthesis gas product stream in the CO conversion zone under CO conversion conditions into an $H_2$-enriched and CO-depleted CO conversion product stream, discharging the CO conversion product stream from the CO conversion zone,
  d) introducing the CO conversion product stream into a gas scrubbing zone operating according to a physical gas scrubbing process with methanol as the absorption medium in which the methanol is recirculated and continuously regenerated, discharging a pure synthesis gas product stream depleted of acidic gas constituents such as $CO_2$ and $H_2S$ from the gas scrubbing zone, discharging one or more material streams enriched in acidic gas constituents such as $CO_2$ and $H_2S$ from the gas scrubbing zone, discharging a liquid methanol purge stream laden with trace impurities from the gas scrubbing zone,
wherein the methanol purge stream is at least partially recycled and added to the raw synthesis gas product stream before introduction into the CO conversion zone.

Plant for producing a purified and converted synthesis gas containing hydrogen ($H_2$) and carbon monoxide (CO), comprising the following constituents, constructional elements and functional groupings in fluid connection with one another:
  a) a synthesis gas generation stage, means for providing a carbon-containing gasification or reforming input stream and means for introducing said stream into the synthesis gas generation stage,
  b) means for reacting the carbon-containing gasification or reforming input stream in the synthesis gas generation stage under synthesis gas generation conditions to afford a raw synthesis gas product stream which contains not only the primary constituents $H_2$ and CO but also carbon dioxide ($CO_2$) and hydrogen sulfide ($H_2S$) as acidic synthesis gas constituents as well as secondary and trace components such as carbonyl sulfide (COS), ammonia ($NH_3$), hydrogen cyanide (HCN), mercaptans (RSH), metal carbonyls, means for discharging the raw synthesis gas product stream from the synthesis gas generation stage,
  c) a CO conversion zone (CO shift zone), means for introducing the raw synthesis gas product stream into the CO conversion zone, means for converting the raw synthesis gas product stream in the CO conversion zone under CO conversion conditions into an $H_2$-enriched and CO-depleted CO conversion product stream, means for discharging the CO conversion product stream from the CO conversion zone,
  d) a gas scrubbing zone operating according to a physical gas scrubbing process with methanol as the absorption medium in which the methanol is recirculated and continuously regenerated, means for introducing the CO conversion product stream into the gas scrubbing zone, means for discharging a pure synthesis gas product stream depleted of acidic gas constituents such as $CO_2$ and $H_2S$ from the gas scrubbing zone, means for discharging one or more material streams enriched in acidic gas constituents such as $CO_2$ and $H_2S$ from the gas scrubbing zone, means for discharging a liquid methanol purge stream laden with trace impurities from the gas scrubbing zone, wherein said plant further comprises means which make it possible for the methanol purge stream to be at least partially recycled and added to the raw synthesis gas product stream before introduction into the CO conversion zone.

Fluid connection between two regions is to be understood as meaning any type of connection whatsoever which makes it possible that a fluid, for example the liquid absorption medium, can flow from the one to the other of the two regions, neglecting any interposed regions, component parts, valves or apparatuses.

A gasification or reforming input stream is to be understood as meaning a material stream comprising carbon carriers convertible into synthesis gas constituents under gasification or reforming conditions.

Carbon carriers are to be understood as meaning any substances or substance mixtures containing carbon in a form convertible into synthesis gas constituents under synthesis gas generation conditions. Examples include natural gas, bituminous coal, lignite, biomass and also the carbon-containing wastes or by-products, for example refinery residues or pyrolysis oils.

The term biomass is to be understood as meaning the constituent material of living organisms or parts thereof. In the wider sense it is also to be understood as fossil biomass such as for example coal, crude oil or natural gas.

A synthesis gas generation stage is to be understood as meaning any apparatuses/process sections suitable for generating a gas mixture containing hydrogen and carbon monoxide, i.e. synthesis gas, from an input stream containing carbon carriers. For conversion of non-gaseous carbon carriers into synthesis gas, the operation is often described as gasification, whereas, when using natural gas, it is more usual to refer to reforming, for example—depending on the process mode—to steam reforming or autothermal reforming (ATR) or—in the absence of solid catalysts—to partial oxidation (PDX).

A CO conversion zone is to be understood as meaning a spatially delimited region configured such that the CO conversion reaction may be performed in its interior. To this end the CO conversion zone comprises means for introduction of a synthesis gas stream to be converted and of water as the reaction partner, means for discharging a converted, i.e. enriched in hydrogen and depleted in CO, synthesis gas stream and a catalyst active for the CO conversion reaction. The CO conversion zone may comprise for example a CO conversion reactor, especially also a plurality of CO conversion reactors, which each contain a single catalyst bed or else especially a plurality of catalyst beds. The CO conversion reactors and/or the catalyst beds may be traversed consecutively and/or simultaneously by the synthesis gas stream to be converted.

Synthesis gas generation conditions/CO conversion conditions are to be understood as meaning physicochemical conditions which allow an at least partial, preferably industrially relevant, for example largely complete, reaction of the carbon carriers present in the carbon-containing gasification or reforming input stream with gasification agents such as oxygen, air and/or steam to afford synthesis gas constituents or conversion of the carbon monoxide present in the raw synthesis gas into carbon dioxide and hydrogen. In both cases they are known per se from the prior art and comprise not only the supply of the gasification agent(s) but also the establishment of suitable temperatures. The precise synthesis gas generation conditions/CO conversion conditions will be suitably chosen by a person skilled in the art according to the carbon carriers to be converted/the desired degree of conversion. Especially in the case of CO conversion said person will also consider the influence of the physicochemical conditions on the position of the reaction equilibrium in conjunction with the reaction kinetics.

A means is to be understood as meaning a thing which makes it possible to achieve or is helpful to the achievement of a goal. In particular, means for performing a certain process step are to be understood as meaning all physical articles which a person skilled in the art would contemplate in order to be able to perform this process step. For example, as means for introducing or discharging a material stream, a person skilled in the art will contemplate all transporting and conveying apparatuses, for example pipelines, pumps, compressors, valves, which on account of his knowledge of the art appear necessary or useful to him for performing this process step.

Pressures reported in the unit bar(a) relate to absolute pressure in bar absolute. Pressures reported in the unit bar(g) relate to positive pressure in bar.

The invention is based on the finding that the CO conversion catalyst is also active for efficient decomposition of the methanol, i.e. cracking of the methanol into the synthesis gas constituents CO and $H_2$ in the reverse of the methanol synthesis equation:

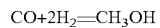

$$CO + 2H_2 = CH_3OH$$

Accordingly the methanol discharged from the gas scrubbing process may advantageously be recycled into the synthesis gas pool and thus utilized as a feedstock. This surprisingly also effects decomposition of unwanted disruptive components/trace impurities, for example of hydrogen cyanide.

BRIEF DESCRIPTION OF THE DRAWINGS

For a further understanding of the nature and objects for the present invention, reference should be made to the following detailed description, taken in conjunction with the accompanying drawings, in which like elements are given the same or analogous reference numbers and wherein.

DETAILED DESCRIPTION OF THE PREFERRED EMBODIMENTS

Figure 1:
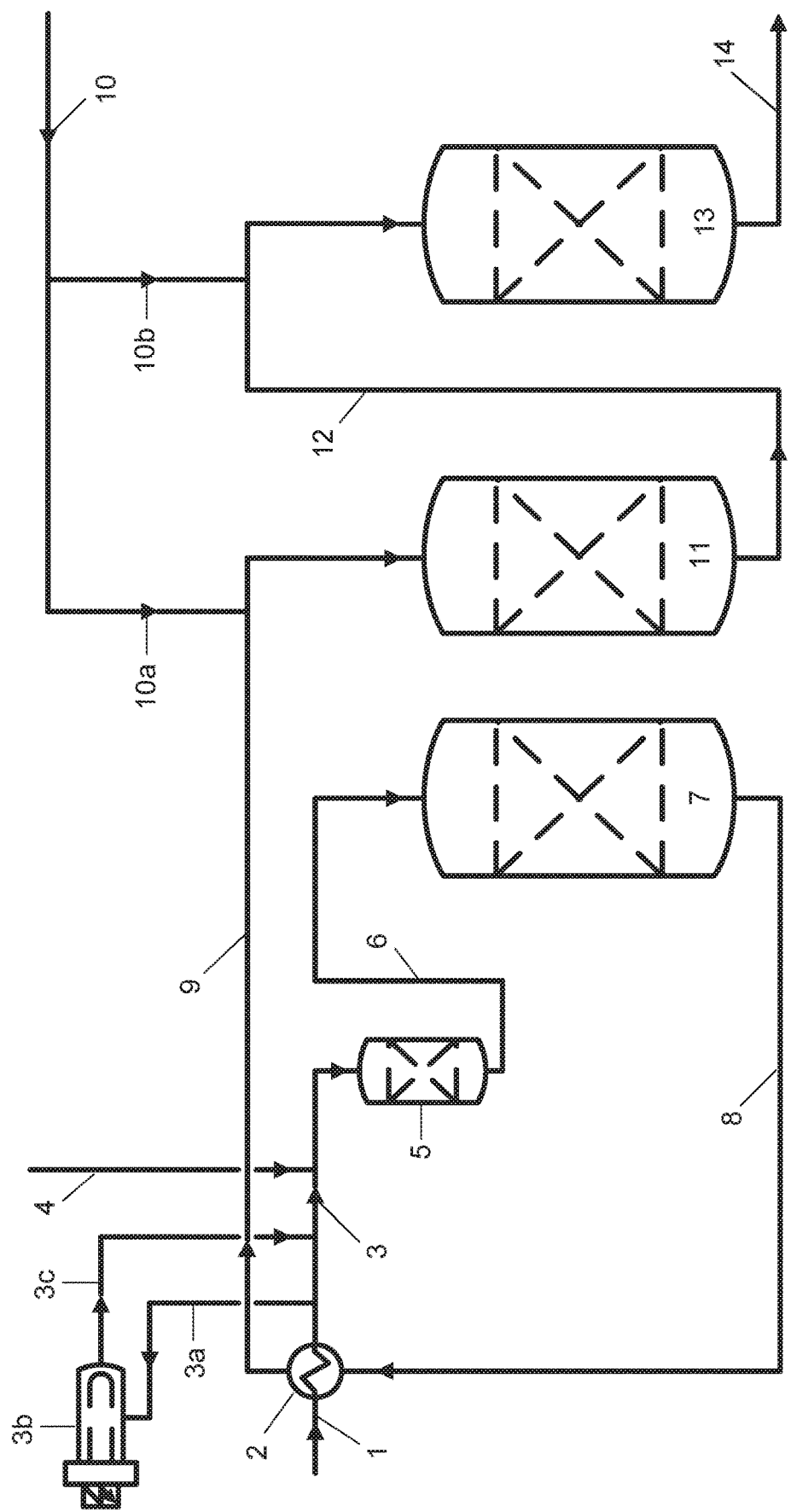
FIG. 1 is a schematic representation of a process/of a plant according to prior art.

One particular embodiment of the process according to the invention is characterized in that before introduction into the CO conversion zone the raw synthesis gas product stream passes through a protective bed filled with an adsorbent or absorbent selective for metal carbonyls, wherein the methanol purge stream is added to the raw synthesis gas product stream upstream of the protective bed. This prevents the metal carbonyls getting into the CO conversion zone and then poisoning the CO conversion catalyst present there.

When the methanol purge stream is added to the raw synthesis gas product stream to the raw synthesis gas product stream upstream of the protective bed a particular embodiment provides that the methanol purge stream is added to the raw synthesis gas product stream in liquid form. This has the advantage that the protective bed simultaneously acts as a static mixer, thus ensuring a homogeneous distribution of the methanol purge stream in the raw synthesis gas product stream.

When the methanol purge stream is added to the raw synthesis gas product stream upstream of the protective bed an alternative embodiment provides that the methanol purge stream is evaporated before or during its addition to the raw synthesis gas product stream, wherein the evaporation heat is supplied by direct or indirect heat exchange with the raw synthesis gas product stream. The methanol purge stream may accordingly be added to the raw synthesis gas product stream directly in liquid form, for example by injection or spraying, and is evaporated by direct heat exchange with the raw synthesis gas product stream. The methanol purge stream may alternatively also be evaporated before combination with the raw synthesis gas product stream, wherein the evaporation heat may for example be supplied to the raw synthesis gas product stream in a suitable heat exchanger by means of indirect heat exchange. In both cases the traversed protective bed has a homogenizing effect on the obtained gas mixture.

A further embodiment of the process according to the invention is characterized in that the CO conversion zone operates according to the principle of raw gas conversion (raw gas shift). The catalysts used here are active for the conversion of methanol into synthesis gas constituents and insensitive towards any trace components and impurities in the methanol purge stream.

A further particular embodiment of the process according to the invention is characterized in that the CO conversion zone comprises a plurality of regions filled with one or more catalysts active for the raw gas conversion. Multi-stage performance of the CO conversion has proven advantageous in industry since this provides more degrees of freedom for establishing the reaction conditions optimal in each case in the individual catalyst beds, for example by intermediate cooling or precise feed introduction between the individual catalyst beds. Also advantageous is that in the case of impurities present in the methanol purge stream that are also catalyst poisons it is especially the first catalyst bed in the flow direction that is affected and therefore only this bed, rather than the entire catalyst inventory of the CO conversion zone, may require regeneration or replacement.

In a further particular embodiment of the process according to the invention it is provided that the gas scrubbing zone comprises a hot regeneration apparatus for regeneration of methanol laden with acidic gas constituents, wherein the liquid methanol purge stream laden with trace impurities is obtained from the bottoms product and/or the reflux from the hot regeneration apparatus and is discharged from the hot regeneration apparatus. Since the trace impurities accumulate particularly strongly in the bottom of the hot regeneration apparatus this is a particularly suitable position for withdrawal of the methanol purge stream.

One particular embodiment of the plant according to the invention is characterized in that it further comprises a protective bed filled with an adsorbent or absorbent selective for metal carbonyls and arranged upstream of the CO conversion zone so that the raw synthesis gas product stream passes through the protective bed before introduction into the CO conversion zone and means allowing the methanol purge stream to be added to the raw synthesis gas product stream upstream of the protective bed. This prevents the metal carbonyls getting into the CO conversion zone and then poisoning the CO conversion catalyst present there.

When the methanol purge stream is added to the raw synthesis gas product stream upstream of the protective bed a particular embodiment of the plant according to the invention provides that it comprises means allowing the methanol purge stream to be added to the raw synthesis gas product stream in liquid form. This has the advantage that the protective bed simultaneously acts as a static mixer, thus ensuring a homogeneous distribution of the methanol purge stream in the raw synthesis gas product stream.

When the methanol purge stream is added to the raw synthesis gas product stream upstream of the protective bed an alternative embodiment of the plant according to the invention provides that it comprises means allowing the methanol purge stream to be evaporated before or during its addition to the raw synthesis gas product stream, wherein the evaporation heat is supplied by direct or indirect heat exchange with the raw synthesis gas product stream. The methanol purge stream may accordingly be added to the raw synthesis gas product stream directly in liquid form, for example by injection or spraying, and is evaporated by direct heat exchange with the raw synthesis gas product stream. The methanol purge stream may alternatively also be evaporated before combination with the raw synthesis gas product stream, wherein the evaporation heat may for example be supplied to the raw synthesis gas product stream in a suitable heat exchanger by means of indirect heat exchange. In both cases the traversed protective bed has a homogenizing effect on the obtained gas mixture.

A further embodiment of the plant according to the invention is characterized in that the CO conversion zone operates according to the principle of raw gas conversion (raw gas shift). The catalysts used here are active for the conversion of methanol into synthesis gas constituents and insensitive towards any trace components and impurities in the methanol purge stream.

A further particular embodiment of the plant according to the invention is characterized in that the CO conversion zone comprises a plurality of regions filled with one or more catalysts active for the raw gas conversion. Multi-stage performance of the CO conversion has proven advantageous in industry since this provides more degrees of freedom for establishing the reaction conditions optimal in each case in the individual catalyst beds, for example by intermediate cooling or precise feed introduction between the individual catalyst beds. Also advantageous is that in the case of impurities present in the methanol purge stream that are also catalyst poisons it is especially the first catalyst bed in the flow direction that is affected and therefore only this bed, rather than the entire catalyst inventory of the CO conversion zone, may require regeneration or replacement.

In a further particular embodiment of the plant according to the invention it is provided that the gas scrubbing zone comprises a hot regeneration apparatus for regeneration of methanol laden with acidic gas constituents, wherein the liquid methanol purge stream laden with trace impurities is obtained from the bottoms product and/or the reflux from the hot regeneration apparatus and is discharged from the hot regeneration apparatus. Since the trace impurities accumulate particularly strongly in the bottom of the hot regeneration apparatus this is a particularly suitable position for withdrawal of the methanol purge stream.

Further features, advantages and possible applications of the invention are also apparent from the following description of a working and numerical example and from the drawings. All the features described and/or depicted, on their own or in any combination, form the subject-matter of the invention.

In both figures the graphic representation is in each case limited to the plant part relating to CO conversion (CO shift).

In the embodiment of a process/a plant according to the prior art shown schematically in FIG. 1 raw synthesis gas is supplied from a plant for coal gasification (not shown) via conduit 1 and heated in indirect heat exchange against hot product gas from the first reactor of the multi-stage CO conversion zone (CO shift zone) in heat exchanger 2. The raw synthesis gas contains not only the wanted synthesis gas constituents hydrogen and carbon monoxide but also inter alia the unwanted, acidic synthesis gas constituents carbon dioxide and hydrogen sulfide and also further organic and inorganic sulfur compounds such as for example carbonyl sulfide (COS), ammonia ($NH_3$), hydrogen cyanide (HCN), mercaptans (RSH), metal carbonyls. The heated raw synthesis gas is discharged from the heat exchanger 2 via conduit 3.

Since hot CO conversion product gas is not yet available upon startup of the process/the plant the raw synthesis gas supplied from the coal gasification is passed via conduit 3$a$ to the startup heater 3$ab$, heated therein and recycled to conduit 3 via conduit 3$c$.

Supplied as a reaction partner for the CO conversion via conduit 4 to the heated raw synthesis gas supplied via conduit 3 is water in the form of high-pressure steam. The thus obtained reaction mixture is then supplied via conduit 3 to a protective bed filled with an adsorbent or absorbent selective for metal carbonyls and contained in a vessel 5. This removes the metal carbonyls from the reaction mixture so that poisoning of the downstream catalyst stages can no longer occur.

Via conduit 6 the reaction mixture freed of carbonyls is discharged from the vessel 5 and supplied to the first reactor 7 of a multistage, presently three-stage, CO conversion zone 7, 11, 13. In the present example this is a raw gas conversion/sour gas shift. Each reaction stage consists of a fixed bed reactor filled with a dumped bed of a solid, granular catalyst active for the sour gas shift. The commercially available catalyst is based on the metals cobalt and molybdenum as the active components. The reaction conditions to be employed are therefore specified by the supplier and known to those skilled in the art.

Since the CO conversion reaction in reactor 7 proceeds exothermically the CO conversion product gas from the first reaction stage exits reactor 7 at a temperature higher than the entry temperature. The product gas is therefore discharged from reactor 7 by means of conduit 8 and supplied to the shell side of the heat exchanger 2 where it heats the raw synthesis gas supplied via conduit 1 in indirect heat exchange and is therefore itself cooled. The thus cooled CO conversion product gas from the first reaction stage is discharged from the heat exchanger 2 via conduit 9, mixed with evaporated boiler feed water supplied via conduits 10 and 10$a$ and then supplied to the second reactor 11 of the three stage CO conversion zone 7, 11, 13. The above applies equally to the reactor type of reactor 11 and the type of the catalyst employed.

In reactor 11 the CO conversion product gas from the first reaction stage is further converted to the CO conversion products $H_2$ and $CO_2$, wherein the conversion is less than that in reactor 7 and the reaction is therefore also less strongly exothermic. The conversion product gas from the second reaction stage is therefore discharged from reactor 11 via conduit 12 and supplied to the third reaction stage formed by reactor 13 without further heat exchange. Before introduction into reactor 13 the conversion product gas from the second reaction stage is supplied via conduits 10 and 10$b$ with previously evaporated boiler feed water and mixed therewith.

Reactor 13 forms the final reaction zone of the three-stage CO conversion zone 7, 11, 13. The above applies equally to the reactor type of reactor 13 and the type of the catalyst employed.

Via conduit 14 the gaseous CO conversion end product is discharged from the reactor and supplied to a gas scrubbing zone operating according to a physical gas scrubbing process with methanol as the absorption medium (not shown in the figure). In said zone the methanol is recycled and continuously regenerated in a plurality of regeneration stages which are in the form of flash regeneration or hot regeneration apparatuses.

Discharged from the gas scrubbing zone are a pure synthesis gas product stream depleted in acidic gas constituents such as $CO_2$ and $H_2S$, one or more material streams enriched in acidic gas constituents such as $CO_2$ and $H_2S$ and a liquid methanol purge stream laden with trace impurities. The methanol purge stream is advantageously obtained from the bottoms product and/or the reflux from the hot regeneration apparatus and discharged from the hot regeneration apparatus since the impurities to be removed with the purge stream especially accumulate there. According to the prior art this methanol purge stream is either sent for thermal disposal or else handed over to a disposal company by incineration.

Figure 2:
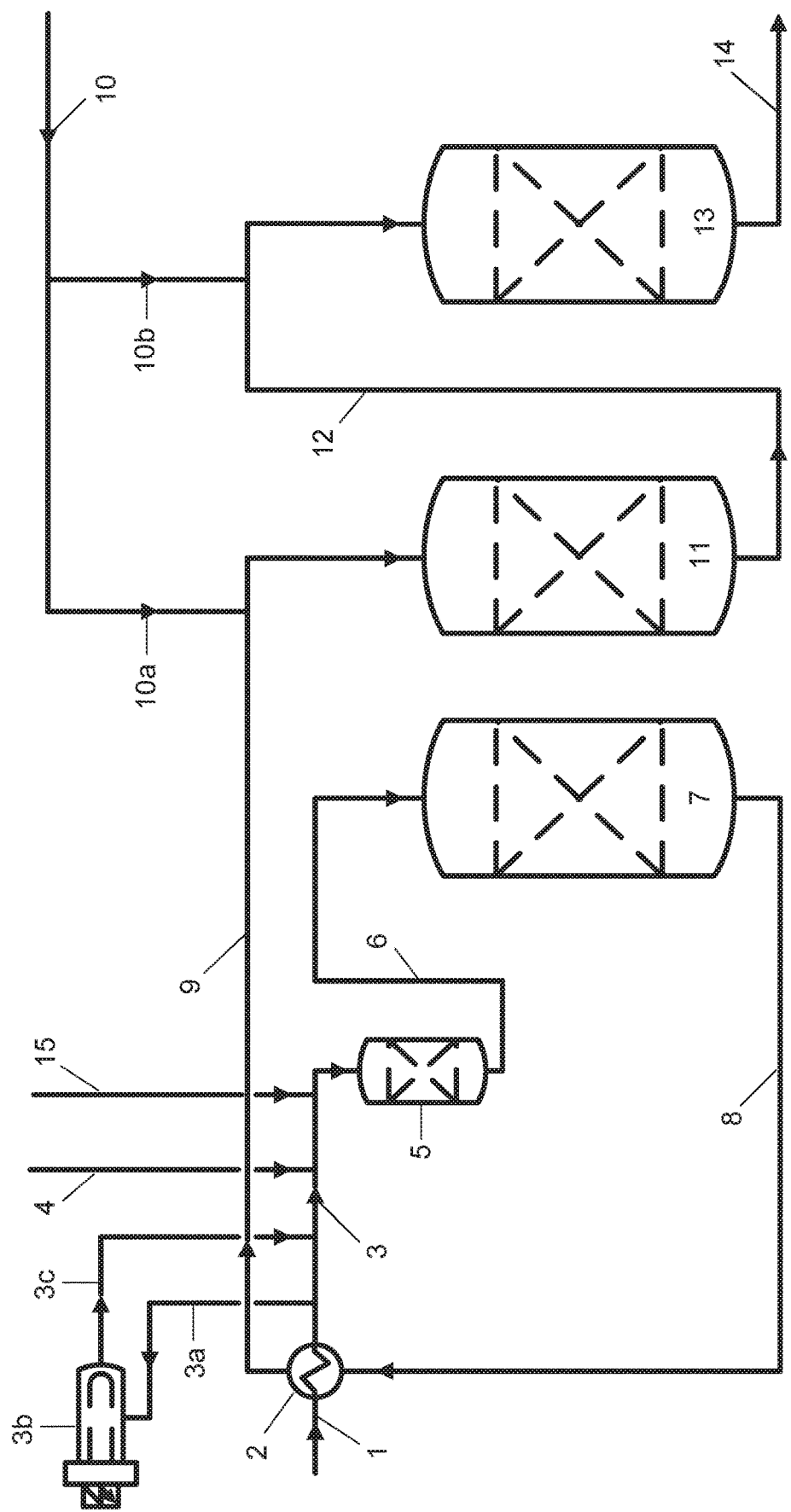
FIG. 2 is a schematic representation of an exemplary embodiment of a process/of a plant according to the invention.

FIG. 2 is a schematic representation of an exemplary embodiment of a process/of a plant according to the invention. The reference numerals 1 to 14 are as defined above.

In contrast to the embodiment of a process/of a plant according to the prior art shown in FIG. 1, in FIG. 2 according to the invention the methanol purge stream obtained from the gas scrubbing zone and laden with impurities is added to conduit 3 upstream of the vessel 5 via conduit 15.

In a particular embodiment of the invention the methanol purge stream is added to conduit 3 via conduit 15 in liquid form. Evaporation is then effected utilizing the heat content of the raw synthesis gas supplied in conduit 3 after heating in heat exchanger 2. Evaporation may optionally be assisted by passing the methanol purge stream added in liquid form through a wick, a drop tray or similar apparatuses for enlarging the liquid surface area arranged at the addition point in the conduit 3. Addition by spraying the methanol purge stream by means of a nozzle protruding into conduit 3 is also possible.

In an alternative particular embodiment of the invention the methanol purge stream is added to conduit 3 via conduit 15 in vapour form. Evaporation is carried out before the addition to conduit 3 by means of an evaporation apparatus arranged in the conduit route of the conduit 15 (not shown in the figure). The evaporation apparatus is advantageously in the form of a heat exchanger or in fluid connection with a heat exchanger in which the evaporation enthalpy is supplied to the methanol purge stream by indirect heat exchange with the raw synthesis gas previously heated in the heat exchanger 2.

In both embodiments it is advantageous when the addition of the methanol purge stream is carried out upstream of the vessel 5 containing the protective bed. This has the advantage that the protective bed simultaneously acts as a static mixer, thus ensuring a homogeneous distribution of the methanol purge stream in the raw synthesis gas product stream.

The table which follows compares quantity flows for important components determined without addition (comparative example) or with addition (invention) of a methanol purge stream to conduit 3 upstream of the vessel 5. Reported in each case are the quantity flows at the entrance to the vessel 5 and in conduit 14, i.e. at the exit of the last CO conversion reactor 13.

Table 1: Quantity flows for important components without and with addition of a methanol purge stream to conduit 3 upstream of vessel 5

TABLE 1

Quantity flows for important components without and with addition of a methanol purge stream to conduit 3 upstream of vessel 5

| Quantity flow kmol/h | Without MeOH purge stream Entrance Vessel 5 Comp. ex. | With MeOH purge stream Entrance Vessel 5 Invention | Without MeOH purge stream Conduit 14 Comp. ex. | With MeOH purge stream Conduit 14 Invention |
|---|---|---|---|---|
| H2 | 2848.23 | 2848.23 | 6021.69 | 6038.62 |
| CO | 3324.91 | 3324.91 | 89.38 | 89.81 |
| CO2 | 352.91 | 352.98 | 3608.72 | 3615.03 |
| H2O | 9008.10 | 9016.65 | 8056.75 | 8057.48 |
| H2S | 44.539 | 44.564 | 46.357 | 46.382 |
| COS | 1.846 | 1.846 | 0.028 | 0.028 |
| NH3 | 16.296 | 16.361 | 18.026 | 18.109 |
| HCN | 1.977 | 1.997 | 0.247 | 0.250 |
| MeOH | 0.240 | 4.871 | 0.351 | 0.357 |

A reduction in the respective quantity flow after passing through the CO conversion zone is clearly apparent especially for the trace impurity hydrogen cyanide (HCN) and the scrubbing medium methanol (MeOH).

INDUSTRIAL APPLICABILITY

The invention provides an integrated process for producing a purified and converted synthesis gas and a corresponding plant in which the methanol purge stream obtained in the gas scrubbing zone and trace impurities present therein may be recycled and catalytically decomposed. This reduces disposal costs and the recycled proportion of the methanol purge stream is utilized as a feedstock within the process.

LIST OF REFERENCE NUMERALS

1 Conduit
2 Heat exchanger
3 Conduit
3a Conduit
3b Start-up heater
3c Conduit
4 Conduit
5 Vessel
6 Conduit
7 Reactor
8 Conduit
9 Conduit
9a Conduit
9b Conduit
10 Conduit
10a Conduit
10b Conduit
11 Reactor
12 Conduit
13 Reactor
14 Conduit
15 Conduit It will be understood that many additional changes in the details, materials, steps and arrangement of parts, which have been herein described in order to explain the nature of the invention, may be made by those skilled in the art within the principle and scope of the invention. Thus, the present invention is not intended to be limited to the specific embodiments in the examples given above.

What is claimed is:

1. A process for producing a purified and converted synthesis gas containing hydrogen ($H_2$) and carbon monoxide (CO), comprising the following process steps:
   a) providing a carbon-containing gasification or reforming input stream and introducing said stream into a synthesis gas generation stage,
   b) reacting the carbon-containing gasification or reforming input stream in the synthesis gas generation stage under synthesis gas generation conditions to afford a raw synthesis gas product stream which contains not only the primary constituents $H_2$ and CO but also carbon dioxide ($CO_2$) and hydrogen sulfide ($H_2S$) as acidic synthesis gas constituents as well as secondary and trace components comprising carbonyl sulfide (COS), ammonia ($NH_3$), hydrogen cyanide (HCN), mercaptans (RSH), metal carbonyls, discharging the raw synthesis gas product stream from the synthesis gas generation stage,
   c) introducing the raw synthesis gas product stream into a CO conversion zone, converting the raw synthesis gas product stream in the CO conversion zone under CO conversion conditions into an $H_2$-enriched and CO-depleted CO conversion product stream, discharging the CO conversion product stream from the CO conversion zone,
   d) introducing the CO conversion product stream into a gas scrubbing zone operating according to a physical gas scrubbing process with methanol as the absorption medium in which the methanol is recirculated and is continuously regenerated, discharging a pure synthesis gas product stream depleted of acidic gas constituents comprising $CO_2$ and $H_2S$ from the gas scrubbing zone, discharging one or more material streams enriched in acidic gas constituents comprising $CO_2$ and $H_2S$ from the gas scrubbing zone, discharging a liquid methanol purge stream laden with trace impurities from the gas scrubbing zone, wherein the methanol purge stream is at least partially recycled and added to the raw synthesis gas product stream before introduction into the CO conversion zone.

2. The process of claim 1, wherein before introduction into the CO conversion zone the raw synthesis gas product stream passes through a protective bed filled with an adsorbent or absorbent selective for metal carbonyls, wherein the methanol purge stream is added to the raw synthesis gas product stream upstream of the protective bed.

3. The process of claim 2, wherein the methanol purge stream is added to the raw synthesis gas product stream in liquid form.

4. The process of claim 2, wherein the methanol purge stream is evaporated before or during its addition to the raw synthesis gas product stream, wherein the evaporation heat is supplied by direct or indirect heat exchange with the raw synthesis gas product stream.

5. The process of claim 1, wherein the CO conversion zone operates according to the principle of raw gas conversion (raw gas shift).

6. The process of claim 1, wherein the CO conversion zone comprises a plurality of regions filled with one or more catalysts active for the raw gas conversion.

7. The process of claim 1, wherein the gas scrubbing zone comprises a hot regeneration apparatus for regeneration of methanol laden with acidic gas constituents, wherein the liquid methanol purge stream laden with trace impurities is obtained from the bottoms product and/or the reflux from the hot regeneration apparatus and is discharged from the hot regeneration apparatus.

\* \* \* \* \*